(12) United States Patent
Holtje et al.

(10) Patent No.: US 7,912,582 B1
(45) Date of Patent: Mar. 22, 2011

(54) ROBOTIC PRESCRIPTION FILLING SYSTEM

(75) Inventors: Bruce E. Holtje, Berkshire, NY (US);
James McGonigal, Binghamton, NY (US)

(73) Assignee: Innovation Associates, Inc., Johnson City, NY (US)

( * ) Notice: Subject to any disclaimer, the term of this patent is extended or adjusted under 35 U.S.C. 154(b) by 717 days.

(21) Appl. No.: 11/879,630

(22) Filed: Jul. 18, 2007

Related U.S. Application Data

(60) Provisional application No. 60/927,411, filed on May 3, 2007.

(51) Int. Cl.
*G06F 17/00* (2006.01)

(52) U.S. Cl. ........ 700/242; 700/241; 700/243; 700/244; 221/126; 221/156; 221/210

(58) Field of Classification Search .................. 700/241, 700/242, 243, 244; 221/126, 156, 210
See application file for complete search history.

(56) References Cited

U.S. PATENT DOCUMENTS

| | | |
|---|---|---|
| 5,638,417 A | 6/1997 | Boyer |
| 5,671,262 A | 9/1997 | Boyer |
| 5,884,006 A | 3/1999 | Frohlich et al. |
| 5,897,024 A * | 4/1999 | Coughlin et al. ............. 221/135 |
| 5,907,493 A | 5/1999 | Boyer et al. |
| 6,006,946 A * | 12/1999 | Williams et al. ............... 700/216 |
| 6,202,923 B1 | 3/2001 | Boyer |
| 6,385,983 B1 * | 5/2002 | Sakki et al. ................... 62/238.7 |
| 6,644,504 B2 * | 11/2003 | Yuyama et al. ................ 221/265 |
| 6,907,493 B2 | 6/2005 | Ryan |
| 6,974,049 B2 * | 12/2005 | Williams et al. ............... 221/120 |
| 7,077,286 B2 * | 7/2006 | Shows et al. ..................... 221/92 |
| 7,228,198 B2 * | 6/2007 | Vollm et al. ..................... 700/235 |
| 7,344,049 B2 * | 3/2008 | Daniels et al. ................... 221/92 |
| 7,563,791 B2 * | 7/2009 | Dixon et al. ................... 514/243 |

OTHER PUBLICATIONS

U.S. Appl. No. 10/319,731.
U.S. Appl. No. 11/325,417.

\* cited by examiner

*Primary Examiner* — Timothy R Waggoner
(74) *Attorney, Agent, or Firm* — Mark Levy; Hinman, Howard & Kattell; David L. Banner (57) ABSTRACT

A self-contained, fully automated system for dispensing medicants into vials. Prescriptions are entered using a built-in workstation. Vials of several sizes are each contained in pre-loaded cassettes. Upon command from a computer, a vial is released and labeled with the prescription information. A robotic system moves the labeled vial to the output chute of one of many automated dispensing units that has previously been commanded to count a predetermined number of tablets, pills, or capsules. The filled vial is robotically moved to an optional capping station where a cap is applied if needed. The vial is then moved to an output region where it is sorted with other prescriptions for a customer. The prescription may be checked using the built-in computer workstation. Optionally, the automated dispensing system may be linked to pharmacy control software.

26 Claims, 12 Drawing Sheets

ROBOTIC PRESCRIPTION FILLING SYSTEM

RELATED APPLICATIONS

The present invention is a continuation-in-part of U.S. provisional patent application Ser. No. 60/927,411, filed May 3, 2007 and claims priority thereof. This application is also related to copending application Ser. Nos. 11/325,987 and 10/319,731 and to U.S. Pat. Nos. 5,638,417; 5,671,262; 5,884,006; and 6,907,493, all of which are included herein by reference.

FIELD OF THE INVENTION

The present invention relates to dispensing pharmaceutical pills, tablets and capsules into vials and, more particularly, to a self-contained, stand-alone pharmacy automation apparatus for dispensing pharmaceuticals into vials, printing labels and applying them to the vials, capping the vials, sorting and grouping orders, all without manual intervention.

BACKGROUND OF THE INVENTION

As the population continues to age and pharmaceutical companies continue to develop more medications for illnesses, it is inevitable that the distribution points for such medications must become more efficient. From large, mail order fulfillment centers that fill tens of millions of prescriptions annually, to national drug store chains to local pharmacies, automation has greatly affected the speed, efficiency and accuracy of prescription distribution.

It is not surprising that automation results in greater profitability for wholesale and retail pharmacy business owners. Reducing manual operations results in lower payrolls, fewer interruptions in workflow, and greater production predictability. In addition, much human error associated with manually filling prescriptions is eliminated. Therefore, the fewer required manual operations and human operators, the more efficient and error-free are prescription fulfillment operations.

With the development of highly accurate robotic mechanisms, including sophisticated hardware and software control systems, servo motors and the like, there should be little need for human operators to perform some of the repetitive tasks still found in pharmacies.

While robotics have been applied to large-scale vial filling operations, heretofore such robotic techniques have not been combined with built-in prescription entry and check features within small, stand-alone units suitable for use in small size pharmacies.

What is needed in modern pharmacies and prescription fulfillment centers is an automated pill, tablet and capsule dispensing system that incorporates robotic mechanisms therein to ensure fast and accurate operations.

DISCUSSION OF RELATED ART

U.S. Pat. No. 6,202,923, issued to Boyer, et al. on Mar. 20, 2001 for AUTOMATED PHARMACY, alleviates the risk posed by a queue of printed labels for prescription vials that occurs at the vial label printer. The method and system eliminate the need for physically transferring paperwork from one site (the imaging station) to another site (the filling station). Elimination of the physical transferring step smoothes the flow of the dispensing operation, improves the throughput of the automated pharmacy, and further, helps to prevent the association of the wrong paperwork with a given prescription.

U.S. Pat. No. 5,907,493, issued to Boyer, et al. on May 15, 1999 for PHARMACEUTICAL DISPENSING SYSTEM, includes a plurality of standardized or universal-type cells disposed in a large array called a module. One or more modules may be disposed in a given pharmacy, and one or more pharmacies may be monitored by a central computer. The system for filling prescriptions includes a graphical interface processing system for monitoring operations of each cell, wherever located, and for sequentially and interactively prompting an operator to perform appropriate, predetermined steps, dependent upon verification of the completion of a prior step in the sequence. In a semi-automatic mode, the pharmacist is directed, by suitable prompts on the computer display screen, to perform the necessary steps and locations in filling each prescription.

The main computer stores information of a plurality of drugs in predetermined, separately-addressable cells, and arranges that information to provide optimum efficiency of pharmacy operations, dependent upon certain parameters: (1) a proximity to a predetermined packaging/shipping location; (2) the probability of future drug access at a predetermined inventory storage location; (3) the size of separately-addressable storage locations; and (4) the location of confusingly similar drugs or dosages. The separately addressable storage locations in inventory have adjustable shelves.

SUMMARY OF THE INVENTION

In accordance with the present invention there is provided an apparatus and method for dispensing pharmaceutical tablets, pills, and capsules, etc. into vials, printing labels and applying them to the vials, optionally capping the vials, and sorting the filled vials either by customer or by other criteria, all without manual intervention. The inventive dispensing system is typically equipped with 140 automated dispensing modules, each typically filled with a different medicant, that may simultaneously and independently count multiple prescriptions. Empty vials of up to three different sizes are stored in refillable, removable cassettes within the novel dispensing system and are automatically selected in accordance with the prescription being filled.

The novel dispensing system includes a built-in user workstation, typically having a touch screen monitor where prescriptions may be entered and checked, the status of all system components and commodities (e.g., medicants, vials, etc.) may be monitored, prescription orders may be tracked, and the overall dispensing system operation may be monitored. Optionally, the automated dispensing system may be coupled to pharmacy automation software such as PharmASSIST® SYMPHONY° software from Innovation Associates, Inc., Johnson City, N.Y. so as to create a end-to-end robotic dispensing and workflow management system.

The inventive dispensing system performs six fundamental operations:

1) counting out the tablets or capsules for a specific prescription from an automated dispensing module loaded with the correct medication;
2) dispensing and orienting a vial of the correct size;
3) printing a label and applying it to a vial;
4) filling the vial with the medicant at the automated dispensing module, and moving the vial to a staging platform;
5) when required, capping the vial; and
6) moving a vial through a door to a transverse conveyor belt, moving it along the transverse conveyor belt, diverting it onto a sorting conveyor belt, and moving it along the sorting conveyor belt where it is accessible to a human operator.

The inventive dispensing system "pipelines" or parallel processes these six independent actions. In other words, each of the aforementioned six actions take place sequentially for any one prescription, but once six prescriptions are in process in the "pipeline," the six actions take place simultaneously, each for a different prescription.

Each of the above actions is typically completed in 15 seconds or less, thereby establishing a continuous filling rate of approximately 240 prescriptions per hour.

It is, therefore, an object of the invention to provide a self-contained, fully automatic pharmaceutical dispensing system.

It is another object of the invention to provide a self-contained, fully automatic pharmaceutical dispensing system that occupies a small footprint.

It is a further object of the invention to provide a self-contained, fully automatic pharmaceutical dispensing system that contains multiple automatic dispensing modules, each typically containing a different medicant.

It is a still further object of the invention to provide a self-contained, fully automatic pharmaceutical dispensing system wherein each automatic dispensing module may count simultaneously with and independently of any other automatic dispensing module.

It is an additional object of the invention to provide a self-contained, fully automatic pharmaceutical dispensing system that has a built-in computer workstation.

It is yet another object of the invention to provide a self-contained, fully automatic pharmaceutical dispensing system that may operate stand-alone or which may be integrated within an automated pharmacy architecture.

It is another object of the invention to provide a self-contained, fully automatic pharmaceutical dispensing system that can store up to three different sizes of empty vials in removable cassettes.

It is still another object of the invention to provide a self-contained, fully automatic pharmaceutical dispensing system wherein the size of vials housed within each removable cassette is automatically communicated to the dispensing system.

It is yet another object of the invention to provide a self-contained, fully automatic pharmaceutical dispensing system wherein the size of vials housed within each removable cassette is communicated to the dispensing system using coded notches, holes, bumps, or the like, disposed in or on an exterior surface of the vial cassette.

It is a further object of the invention to provide a self-contained, fully automatic pharmaceutical dispensing system that has a built-in label printer and label applicator for labeling vials with prescription information.

It is an object of the invention to provide a self-contained, fully automatic pharmaceutical dispensing system that contains a built-in vial capper.

It is another object of the invention to provide a self-contained, fully automatic pharmaceutical dispensing system that sorts filled vials according to a user defined predetermined criteria, for example, by address, or by customer.

It is a further object of the invention to provide a self-contained, fully automatic pharmaceutical dispensing system wherein such operations as vial dispensing, labeling, filling, capping, and sorting are pipelined for optimized prescription throughput.

It is another object of the invention to provide a self-contained, fully automatic pharmaceutical dispensing system that can be used in a non-automatic mode.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF THE PREFERRED EMBODIMENT

The stand-alone automated pharmaceutical dispenser of the present invention is completely self-contained and has a built-in user workstation where prescriptions are entered. Both order status and system status may be monitored. Filled prescriptions are sorted and grouped by customer or similar criteria.

Figure 1:
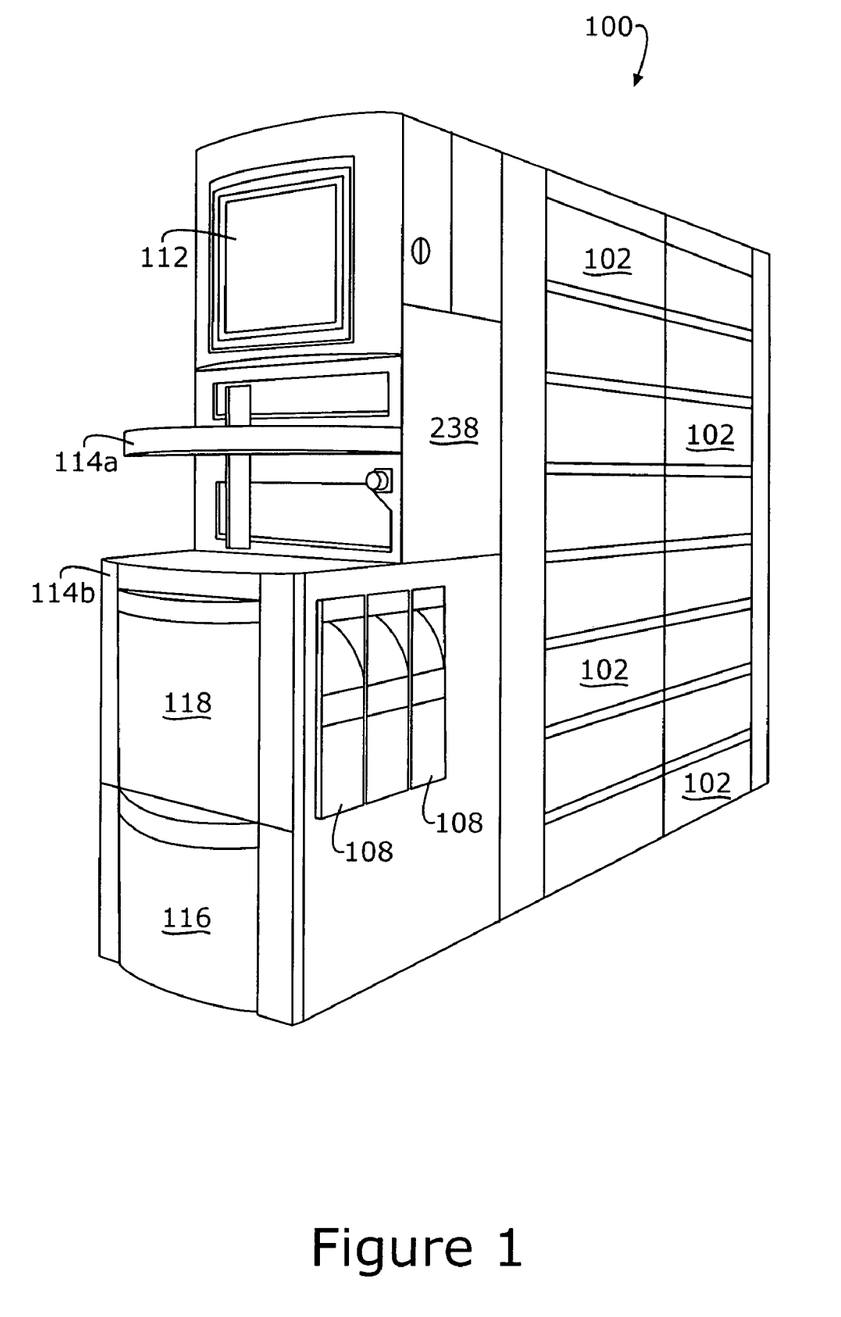
FIG. 1 is a front right perspective, pictorial view of the automated dispensing system of the invention.
Figure 2:
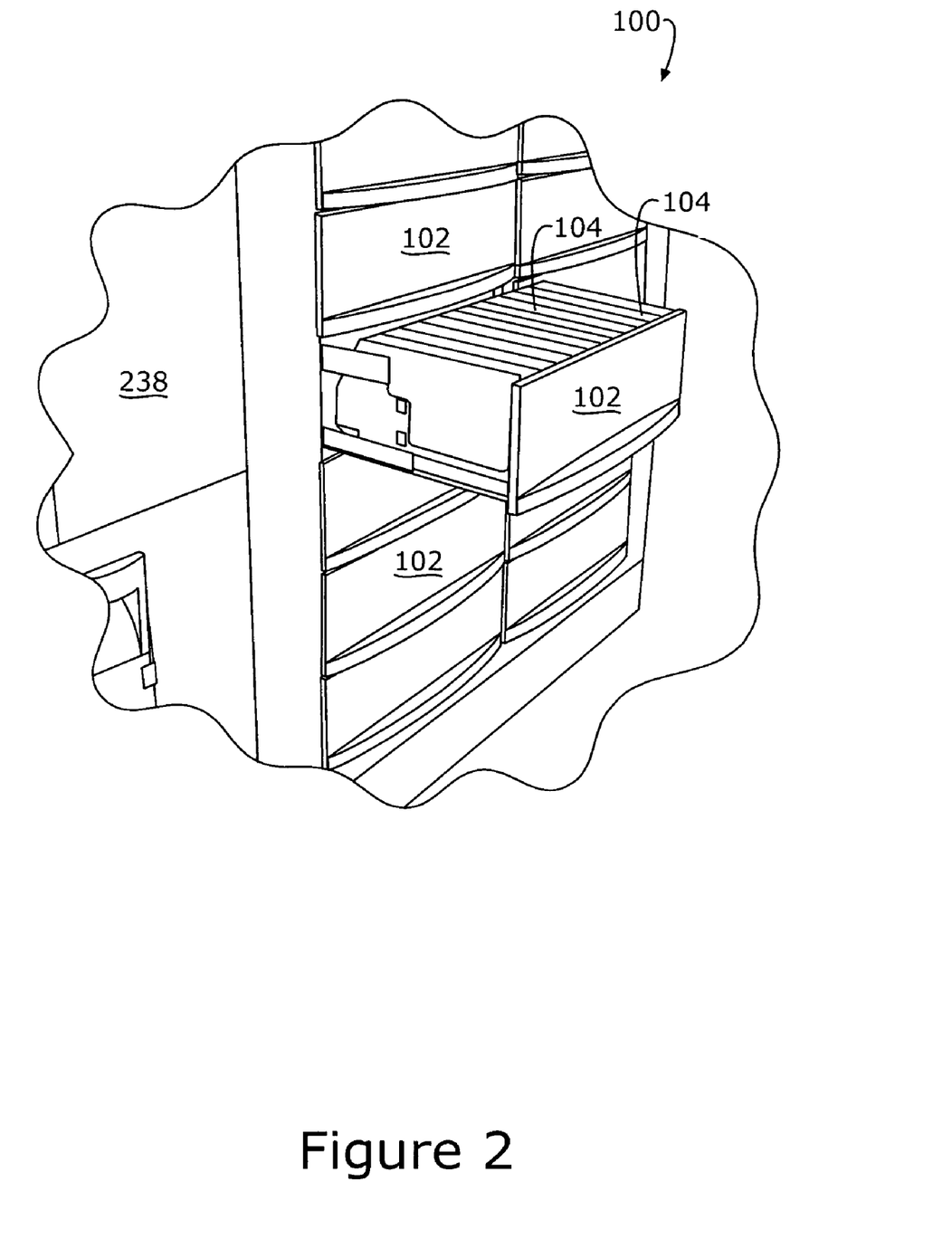
FIG. 2 is a side elevational pictorial view of a portion of the system of FIG. 1 showing a drawer housing a bank of automated dispensing modules withdrawn.

Referring first to FIG. 1, there is shown a front right, perspective, pictorial view of the automated pharmaceutical dispensing system of the invention, generally at reference number 100. FIG. 1 shows dispensing system 100 with all covers closed as configured for normal operation. A series of drawers 102 provides access to the automated pharmaceutical dispensers 104 disposed in slide-out drawers 102 as may be seen in FIG. 2.

Drawers 102 are normally locked in the closed position, and may be unlocked under software control. The operator makes a request through the touch screen monitor 112 and computer 174 (FIG. 7a) which interfaces with programmable logic controller (PLC) 148 (FIG. 7a) which completes any current robotic actions involving pharmaceutical dispensers 104 in the requested drawer 102. In addition, pending robotic actions to pharmaceutical dispensers 104 in the requested drawer 102 are also suspended. PLC 148 then unlocks the requested drawer 102, and turns on an indicator light, not shown, on the drawer 102. An appropriate message may be displayed on the monitor 112 informing the operator, not shown, that the drawer 102 is available to be withdrawn. In this manner the system allows access to the pharmaceutical dispensers 104 for replenishment while other prescriptions are being filled by the machine 100 by pharmaceutical dispensers 104 in others of drawers 102. This simultaneous "run while filling" mode of operation increases throughput and overall efficiency of dispensing system 100.

Figure 3:
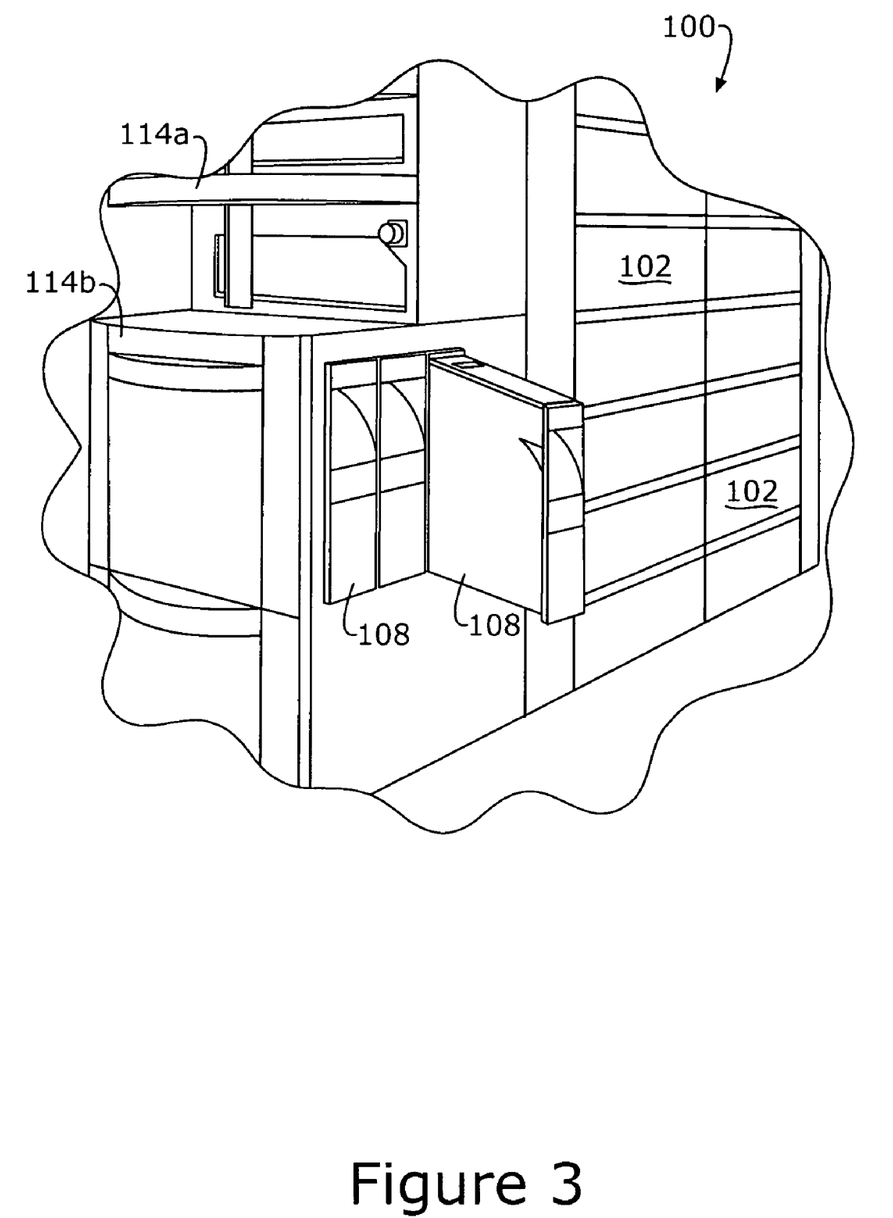
FIG. 3 is a pictorial view of a left side portion of the system of FIG. 1 showing an vial cassette partially withdrawn.

Three removable vial cassettes 108 are disposed in the right-hand side of dispensing system 100. While vial cassettes may be removed and filled remotely from dispensing system 100, they may also be filled locally. In FIG. 3 a vial cassette 108 is shown withdrawn for local filling as discussed in detail hereinbelow.

When present, capping stations 210 (FIG. 7a) are accessible at the right-hand side of dispensing system 100 through one or more access panels 238. Caps, not shown, may be loaded into the capper hopper, not shown. The capper hoppers may tilt or slide out for filling. The capping stations orient and apply the caps. Typically only two sizes of caps will cap all three sizes of vials.

A computer display (i.e., monitor) 112 is positioned on an upper end surface of dispensing system 100. Computer display 112 is typically a touch screen display.

Figure 5:
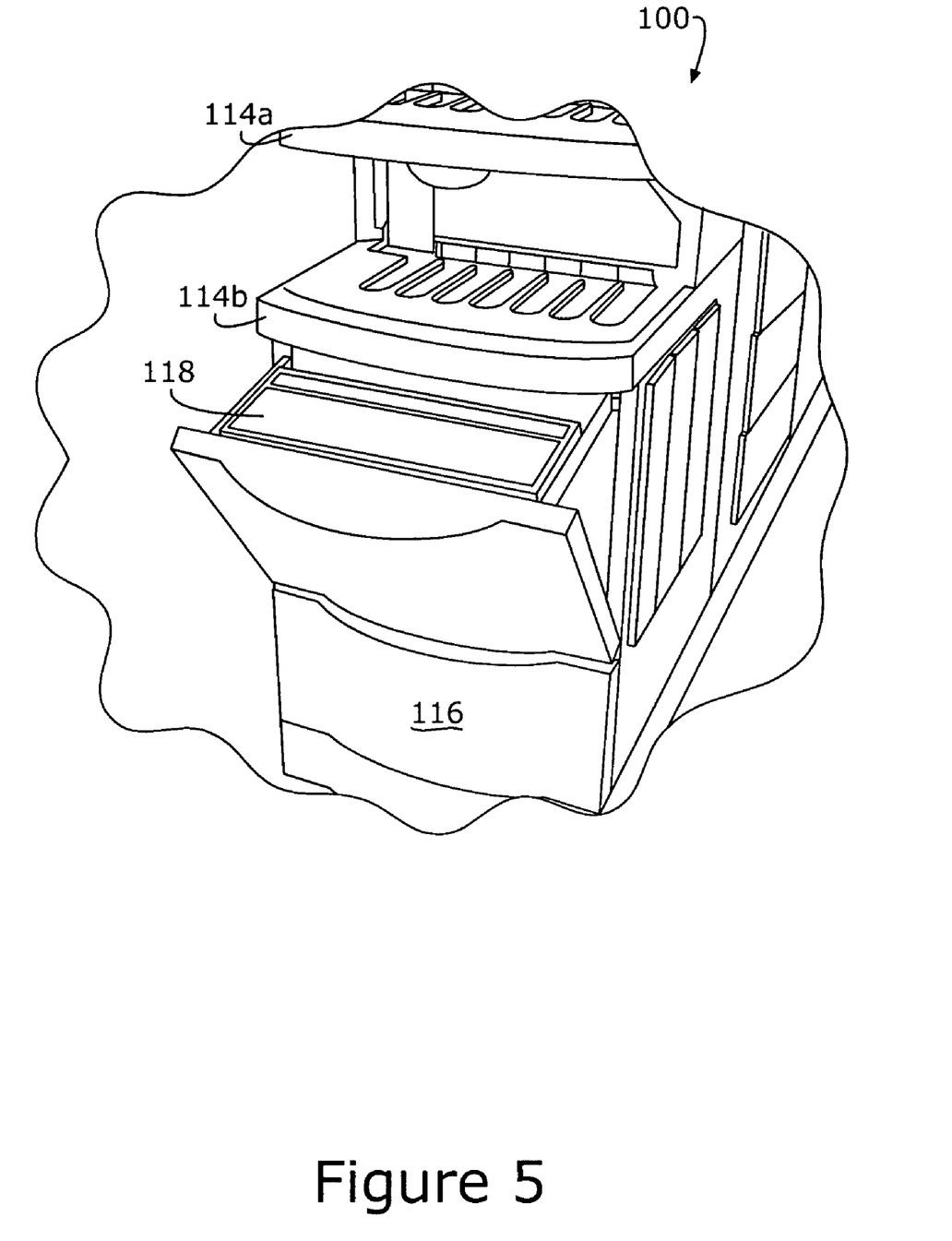
FIG. 5 is a pictorial view of the front of the system of FIG. 1 showing the built-in keyboard open in an operational deployment.

Upper shelf 114a and lower shelf 114b (best seen in FIGS. 5 and 9) project outwardly from the end of dispenser unit 100 below monitor 112. Upper and lower shelves 114a, 114b house conveyor mechanisms not visible in FIG. 1 and discussed in detail hereinbelow.

A tip-out keyboard 118 is disposed in the end of dispensing system 100 below lower shelf 114b. Tip-out keyboard 118 may be clearly seen in FIG. 5.

Figure 6:
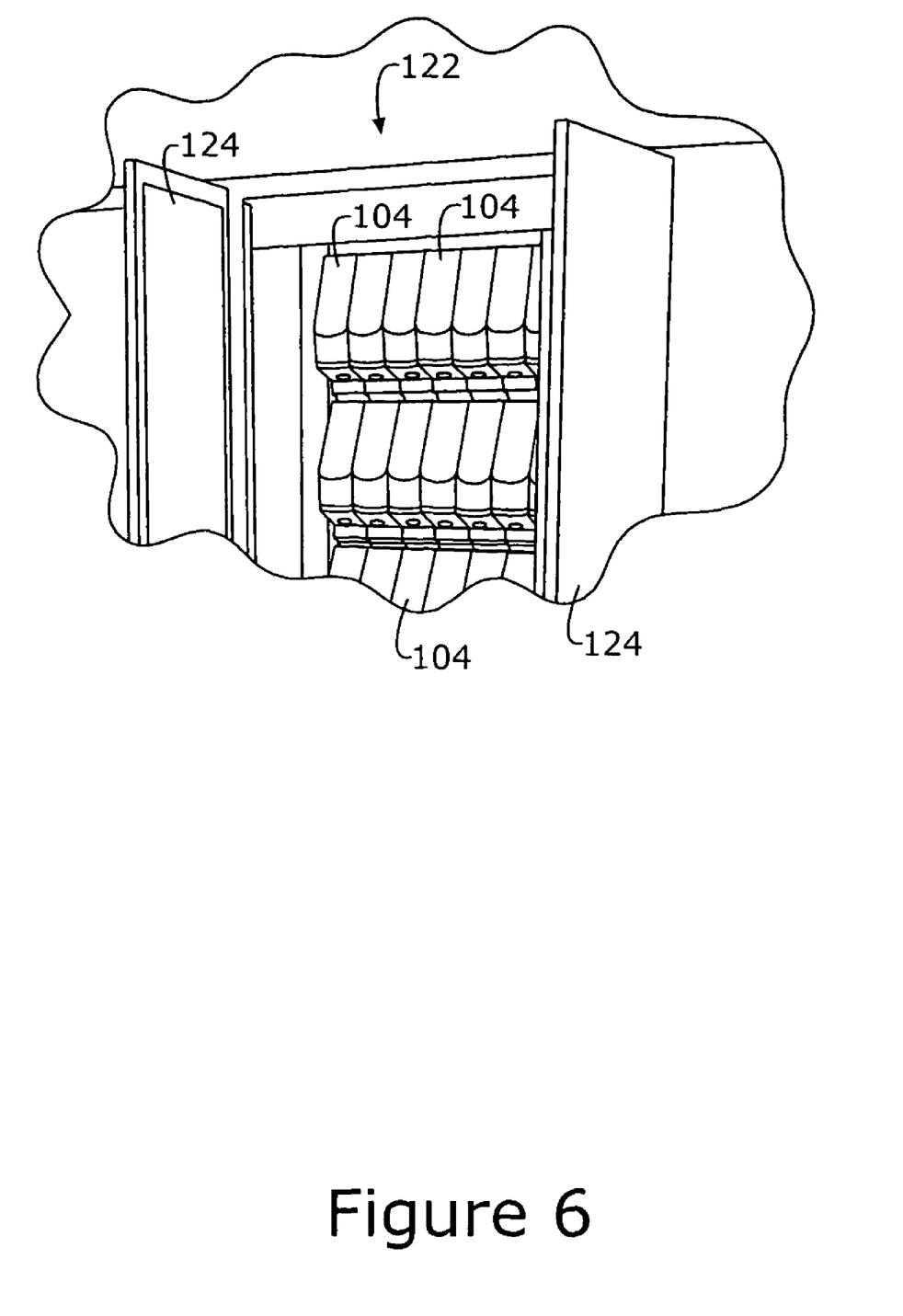
FIG. 6 is a pictorial view of the left side of the system of FIG. 1 with access doors open, revealing the banks of automated dispensing modules.

Referring now to FIG. 6, there is shown a side, elevational, pictorial view of the left side of dispensing system 100 with covers open. A plurality of automated dispensers 104 is arranged in two cabinets 122. Bi-fold doors 124 are shown open, exposing automated dispensers 104. While two cabinets 122 of dispensers 104 are shown, it will be recognized that other numbers of cabinets 122 or other similar devices or systems could readily be substituted therefor. Consequentially, the invention is not limited to the two cabinets 122 chosen for purposes of disclosure but rather includes any number of cabinets or other mounting arrangements for automated dispensers 104. Also, while bi-fold doors 124 have been chosen for purposes of disclosure, it will be recognized than many other configurations of covers may be substituted therefor.

Figure 4A:
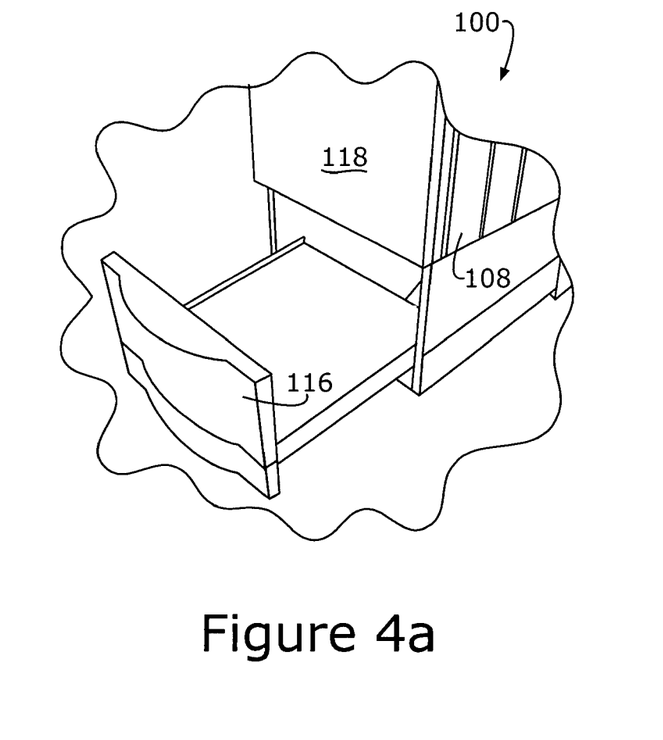
FIGS. 4a and 4b are pictorial views of the lower front region of the system of FIG. 1 showing the label printer drawer in an open position.
Figure 4B:
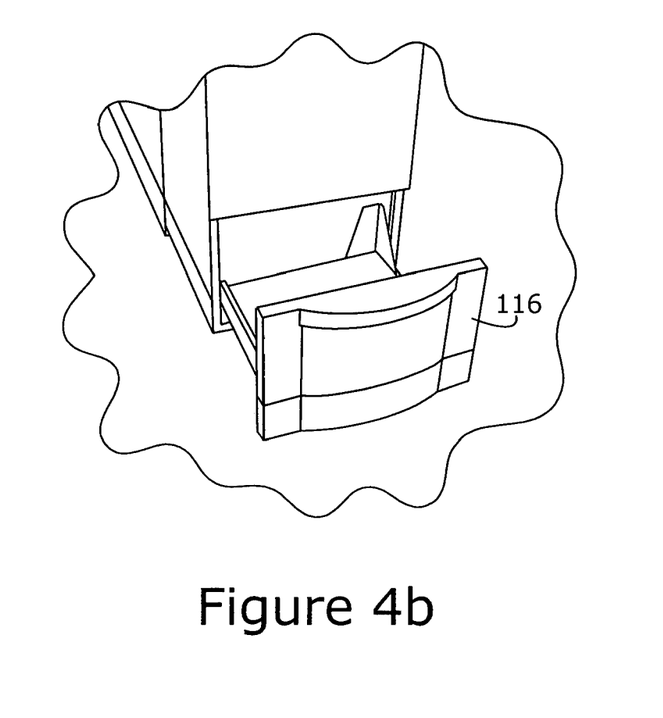

Referring now to FIGS. 4a and 4b, there are shown perspective, pictorial views of label printer 116 withdrawn from dispensing system 100 to allow replenishment of supplies or for service.

Figure 7A:
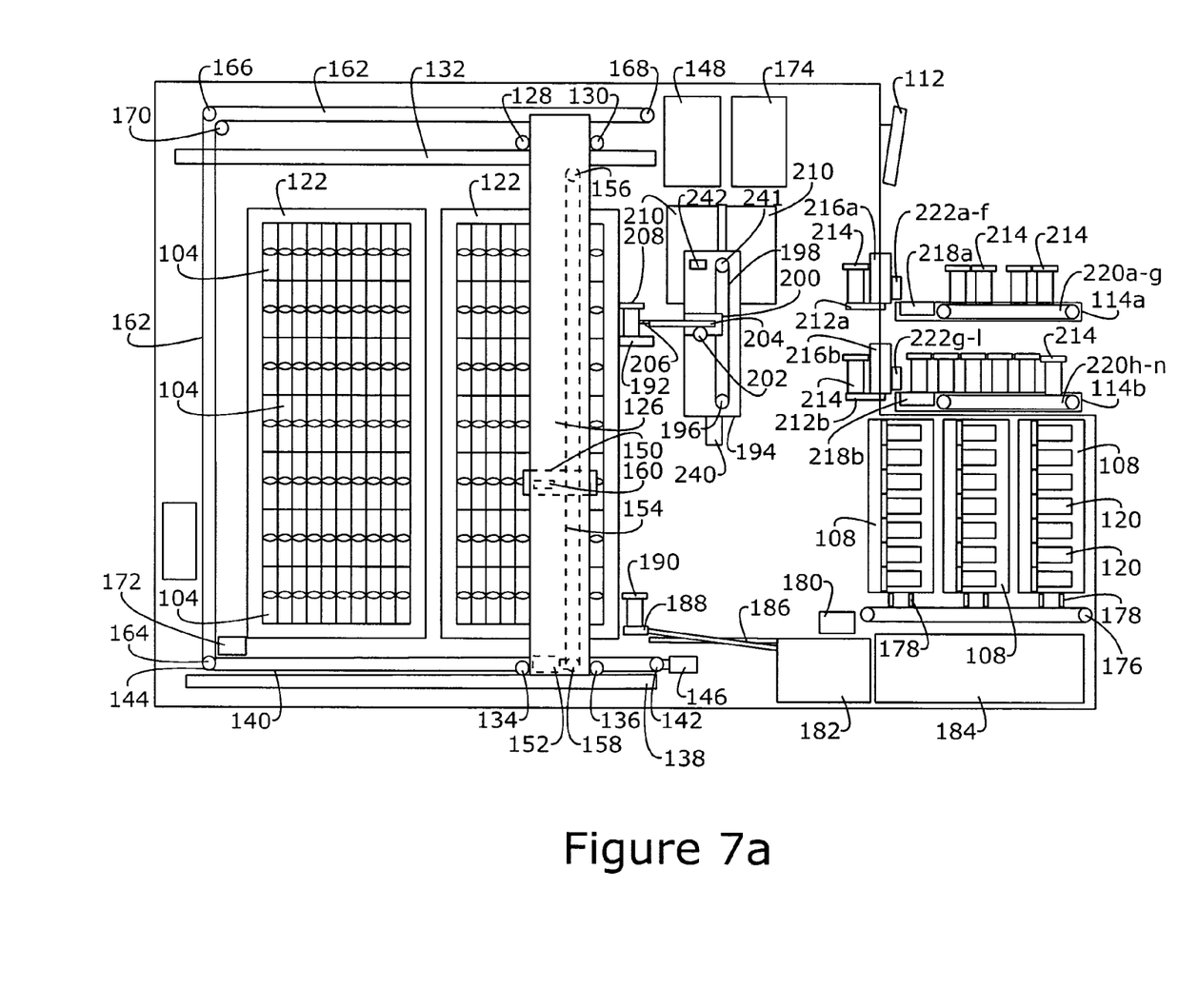
FIGS. 7a and 7b are right side elevational and top schematic views, respectively, of the dispensing system of FIG. 1.
Figure 7B:
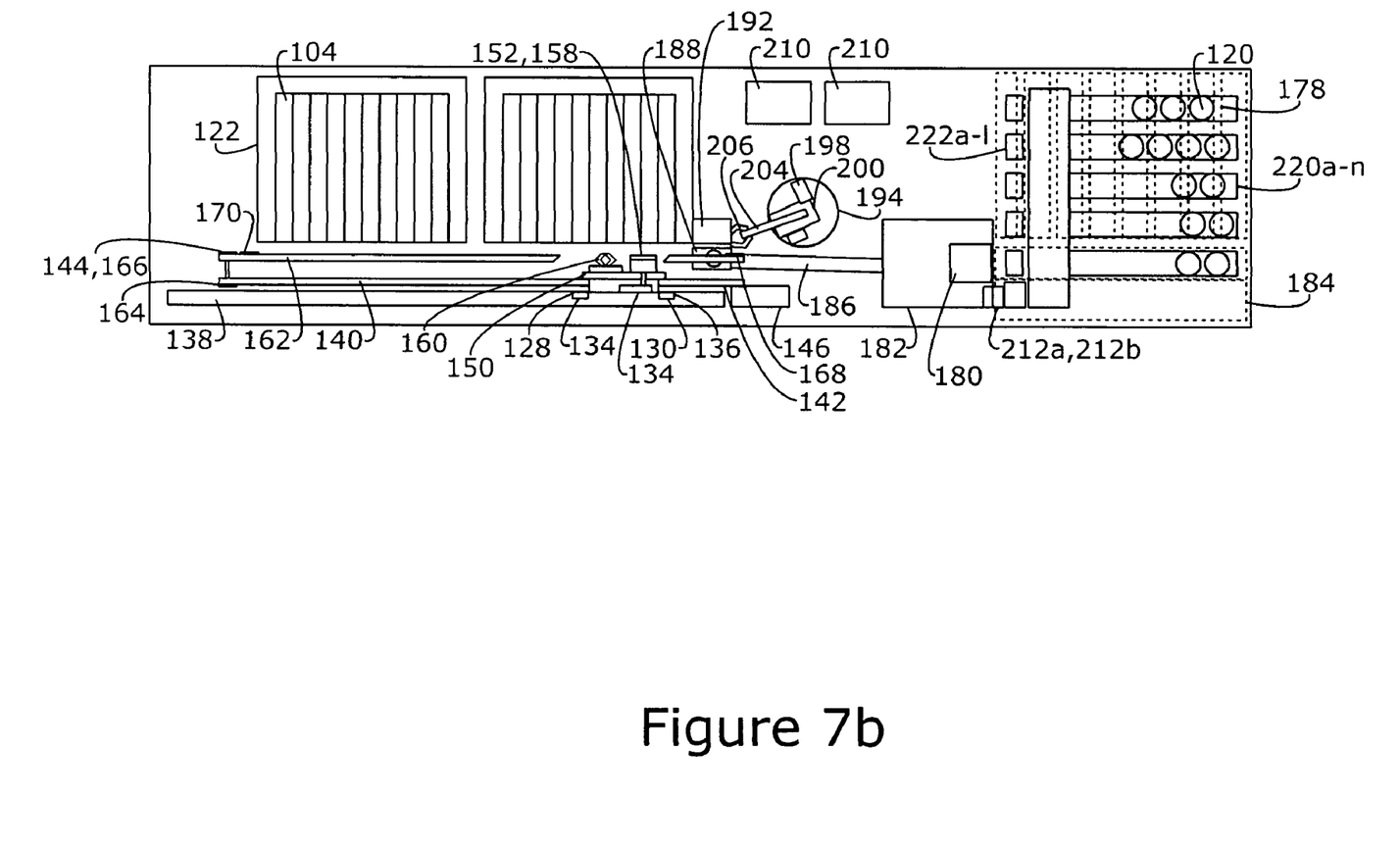

Referring now to FIGS. 7a and 7b, there are shown side elevational schematic and top views, respectively, of dispensing system 100 of the invention. A number of automated dispensers 104 are arranged in rows and columns within cabinets 122. Automated dispensers 104 face outward so that the output chutes thereof, not shown, are accessible to a robotic main gantry 126. Most of the automated dispensers 104 are arranged so that their output chutes, not shown, are in the same plane. However, some of automated dispensers 104 are angled to dispense certain tablets more accurately. Even when so angled, their output chutes, however, are generally in the same plane as the other, non-angled automated dispensers 104. While generally in the same plane as the other, non-angled automated dispensers, the angled automated dispensers require that the vial 190 in the gripper 160 (FIG. 7a) interface the output chute, not shown, of the angled dispenser at an angle compatible with the angle of the automated dispenser 104.

Main gantry 126 is guided at its upper end by two slides 128, 130 which ride on horizontal track 132 and provide stability normal to the plane shown in FIG. 7a. At its lower end, main gantry 126 is supported on multi-wheeled carriages 134, 136 that ride on horizontal track 138, gripping it from both above and below to resist the rotational moments created by the rapid motions of the main gantry 126.

Main gantry 126 is also connected to toothed belt 140, which is carried on toothed wheels 142, 144. In order to keep main gantry 126 synchronized, and to avoid vibrations and oscillations, a second toothed belt 162 is attached to the upper end of vertical member of main gantry 126. Toothed belt 162 is driven by toothed wheel 164, which is separate from, but rigidly attached to, toothed wheel 144. Consequently, toothed wheel 164 rotates with toothed wheel 144. Toothed belt 162 is looped around toothed wheels 164, 166, 168, 170, and back to toothed wheel 164. Toothed belts 140, 162 are rigidly clamped to main gantry 126 and are tension-controlled to maintain necessary tolerances in the positioning of grippers 160.

Toothed wheel 142 is connected to and driven by a first servomotor 146 under the control of a controller 148. Controller 148 is typically a programmable logic controller (PLC) known to those of skill in the controller art and is not further described herein. It will be recognized that many other types of controllers may be used to accomplish the intended function of controller 148. Consequently, as used herein, the term PLC refers to any and all suitable controllers. PLC 148 controls all robotic motions, all aspects of vial dispensing, the application of vial labels, as well as monitoring and controlling all safety locks and interlocks.

A computer 174 is disposed adjacent PLC 148 in an upper front region of automated dispensing system 100. Computer 174 forms the heart of a workstation that provides prescription entry functions and prescription status information, provides prescription label information to label printer 116, provides machine status for dispensing system 100, provides communication control to automated dispensers 104. In addition, computer 174 communicates with other optional workstations involved in pharmacy management when dispensing system 100 is integrated into such systems (i.e., is not operated stand alone).

First servomotor 146 in combination with PLC 148 is used to convey main gantry 126 to a desired horizontal position in front of a selected column of the plurality of automated dispensers 104.

Main gantry 126 includes a carrier 150 adapted for bi-directional vertical movement on main gantry 126. A second servomotor 152, acting cooperatively with PLC 148 and a third toothed belt 154 supported on upper toothed wheel 156 and lower toothed wheel 158, simultaneously positions carrier 150 at a proper height, aligned with a desired row of the plurality of automated dispensers 104.

Mechanism on platform 150 includes a stepper motor, not shown, having a pinion gear, not shown, adapted for interaction with a rack, not shown, on a horizontal member, not shown, of platform 150. The horizontal member may be moved axially away and toward main gantry 126. Grippers 160 are disposed at a distal end of the horizontal member are adapted to grasp and secure a vial 190 during vertical and horizontal (i.e., X-Y axis) motion of main gantry 126. Grippers 160 are attached to the horizontal member, not shown, for moving grippers in and out (i.e., toward and away from the face of automated dispensers 104). This actuator is also connected to and under the control of PLC 148. The actuator typically includes a stepper motor, not shown, and a gear train, not shown, allowing grippers 160 to align vials 190 of different sizes correctly with the discharge chute, not shown, of automated dispensers 104. In addition, grippers 160 include a "wrist motion" allowing a vial 190 to be tilted varying amounts to properly present vials 190 to automated dispensers that are tilted as described hereinabove. In addition, grippers 160 must properly grasp vials 190 on staging platforms (i.e., horizontal surfaces having no tilt). These staging platforms are described hereinbelow.

A compressed air supply 172 is disposed in a rear portion of automated dispensing system 100. Grippers 160, second grippers 206, swinging doors 216a, 216b, diverters 222a-222l, and various other parts of the dispensing system 100 are operated by PLC 148 through the action of miniature pneumatic pistons controlled by electro-pneumatic valves, not shown. Air pressure for these devices is provided by compressed air supply 172. Typically, air is filtered and dried, typically using a simple replaceable desiccant drier prior its distribution throughout dispensing system 100.

Three vial cassettes 108, each holding vials of only a single size, are disposed in a lower, front region of automated dispensing system 100. Empty vials 120 are pre-loaded into cassettes 108. A wide range of vial 120 sizes can be accommodated, but only one size at a time in any one cassette 108. Each vial cassette 108 includes a machine-readable feature, not shown; capable of informing dispensing system 100 of the size, brand, and style of vial 120 contained therein. For example, Owens Illinois, a manufacturer of prescription vials, offers two major styles of vials, "Screw-Loc®" and "1-Clic™".

In the embodiment chosen for purposes of disclosure, each vial cassette 108 has a series of notches or code slots in an exterior region thereof. Switches or other sensors, not shown, are able to "read" the slot pattern to determine the size, brand, and style of the vials 120 contained in the particular cassette 108. It will be recognized that many other methods, such as holes, bumps, optically-read bar codes, color codes, patterns of magnets, RFID tags, etc., are known to those of skill in the art and may be substituted for the code slot system used for purposes of disclosure. Consequently, the invention is not limited to the particular code slot embodiment chosen for purposes of disclosure. Rather, the invention includes any and all methods for identifying the size, brand, and style of a vial 120 within a vial cassette 108 to the dispensing system 100.

Figure 10:
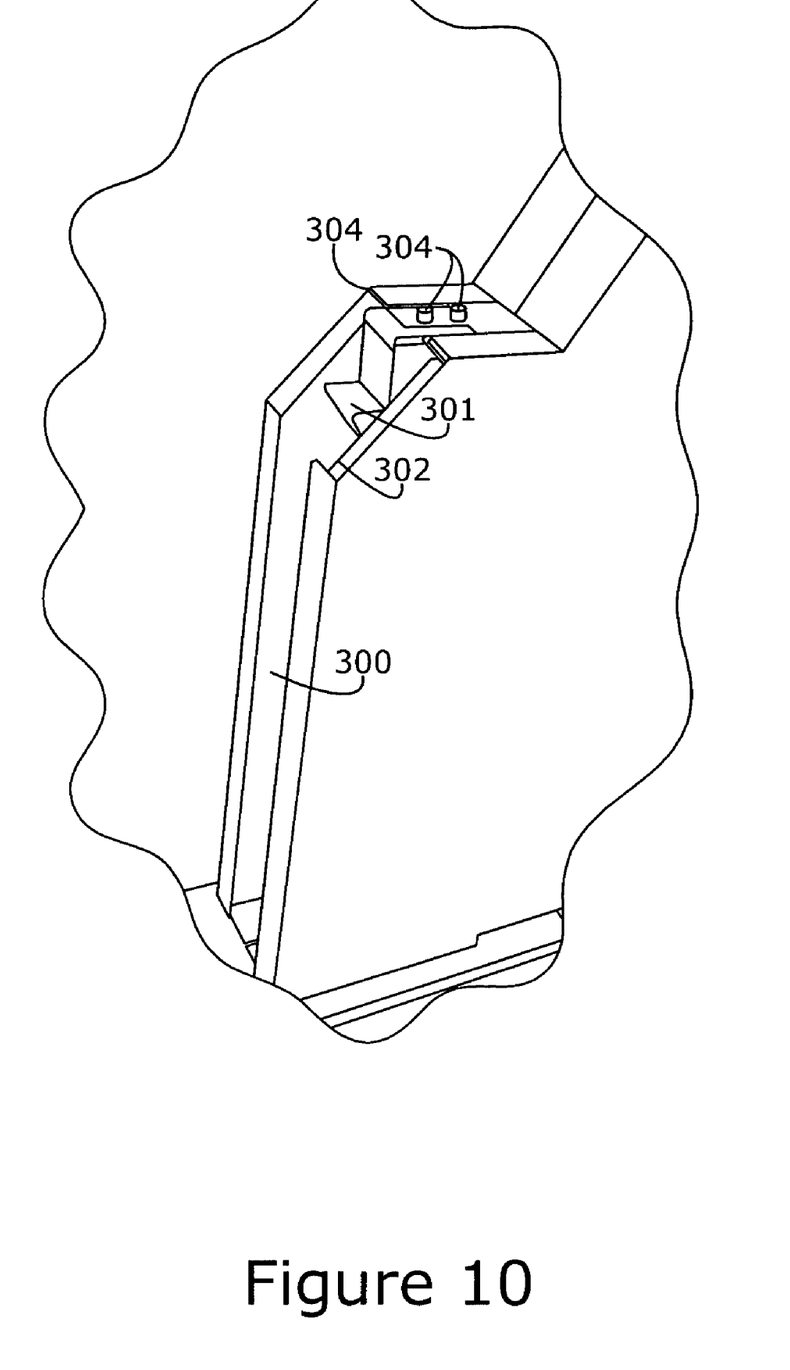
FIG. 10 is a detailed view of the lower portion of a vial cassette.

A pair of ribbed belts 178 is also disposed beneath cassettes 108. Referring now also to FIG. 10, ribs, not shown, on ribbed belts 178 protrude into longitudinal openings 300 in the bottom surfaces of cassettes 108 to agitate and move vials 120, facilitating their release and breaking up vial 120 jams, etc. The ribbed belts 178 move the vials 120 against an angled surface of singulator 301. This forces singulator 301 to climb upward over vial 120. The shape and mass of singulator 301 are chosen such that as the bottom edge climbs over the vial 120, the singulator falls on the vial 120 ejecting it outward, while blocking subsequent vials 120. Singulator 301 is constrained in motion by guide pins 303 operating in slots 304. Singulator 301 is free to move inside the cassette 108 as it is protected from the force of the vials 120 inside cassette 108 by a shield or guard, not shown. Once a vial 120 is singulated and ejected from the cassette 108, vial 120 breaks the beam of an optical sensor, not shown. The signal from the optical sensor is then used to shut off the drive motor, not shown, of ribbed belts 178, thereby completing the selection of a single vial 120 from the selected cassette 108.

Vials 120 are free to move under the influence of gravity inside the cassette 108, and by the motion of ribbed belts 178, but constrained by internal baffles 302 positioned such that the vials 120 cannot rotate, their axis being substantially aligned length-wise to dispenser 100. The internal baffles 302 also allow all cassettes 108 to be the same external width, (thereby any cassette fits in any position of dispensing system 100 but functionally be the correct internal width for the specific vial 120 (size, brand, and style).

The vial cassette 108 can be partially withdrawn from dispenser 100 to expose an opening on the top of vial cassette 108 for reloading vials 120 into the vial cassette 108. The opening is sized and a baffle placed so that the correct sized vial 120 can only be inserted with the vial axis properly aligned cross-wise to the vial cassette 108.

Alternatively, the vial cassette 108 can be completely removed from the dispenser 100 and replaced with another cassette. This replacement can be of the same size or a different sized vial 120. This cassette replacement allows very rapid replenishment of vial supply on the machine, and allows the empty cassettes to be refilled at a more convenient time, and, or, by less skilled labor. This rapid refilling of vials 120 increases the time the dispensing machine 100 is available for dispensing prescriptions.

The internal baffles 302 also provides a vial cassette 108 construction that is adaptable to accommodating vials preloaded into magazines, not shown, for rapid and easy reloading of a cassette.

A horizontal conveyor belt 176 is disposed beneath and adapted to receive vials 120 released from vial cassettes 108. This belt carries the singulated vial to the vial orienting apparatus 180.

A vial orienting apparatus 180 is disposed adjacent an end of horizontal conveyor belt 176. Vial orienting apparatus 180 is adapted to receive a vial 120 from horizontal conveyor belt 176. The vial orienting apparatus 180 probes the vial and detects the current vial orientation, (open-end first or bottom-end first). The vial orienting apparatus 180 then rotates clockwise approximately 90 degrees or counter-clockwise approximately 90 degrees. This rotation ensures that vial 120 is oriented in an upright position with the open top thereof facing up. The vial 120 then drops out of the vial orienting apparatus 180 for vial label application.

Figure 8A:
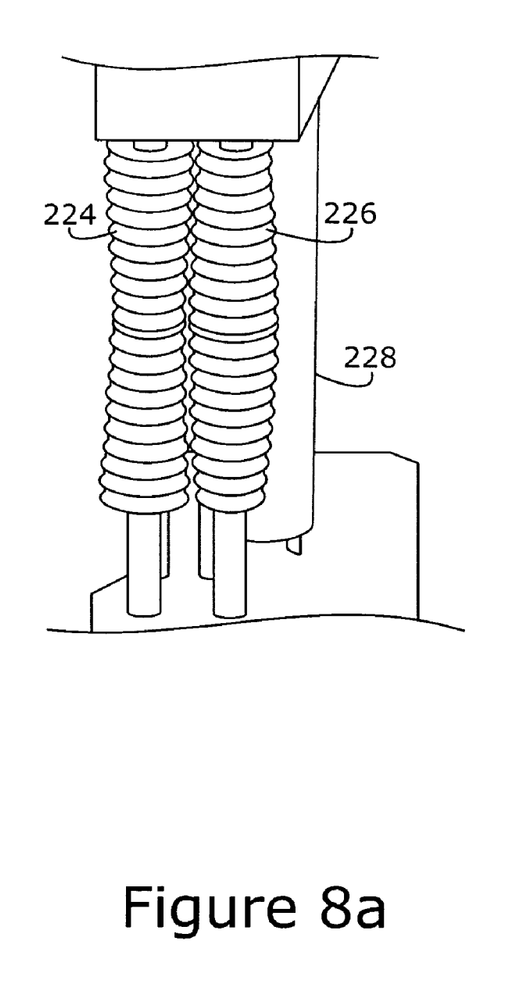
FIG. 8a is a schematic view of the shaping rollers of the label applicator.

A label applicator 182, disposed below vial orienting apparatus 180, receives labels 228 from label printer 184, and applies them to vials 120 after orientation. Self-adhesive labels 228 are produced by a commercial label printer 184, and as the labels 228 are ejected from the printer, the label 228 is peeled off its release liner backing, not shown. Handling the unbacked label 228 which is typically prone to curl (from being wound on a roll) is difficult. Also, it is difficult to get the vial 120 close to the ejected label 228. To ensure that the self-adhesive label 228 is properly positioned, with adequate space between the label ejection point and the vial 120, additional rollers are placed to guide the label 228 must be overcome as the label 228 passes through these additional rollers. This is accomplished as may be seen in FIG. 8a, label 228 is passed through and formed by multiple pairs of shaped rollers, 224, 226 that "cup" or form label 228 with a dihedral which strengthens the label 228 mechanically (i.e., provides rigidity, or beam-strength) that helps assure accurate, stable positioning of label 228 on vial 120. Additionally, these shaped rollers 224, 226 are made with surfaces that are a series of cusps, so only the thin knife edges of the cusps touch the adhesive of the label 228, reducing the contact area to a minimum for control of the dihedral shape. To further increase the reliability of handling these self-adhesive labels 228 through these shaped rollers 224, 226, the rollers 224, 226 themselves are typically made from, or coated with, Polytetrafluoroethylene (PTFE) or similar low surface-energy material.

Figure 8B:
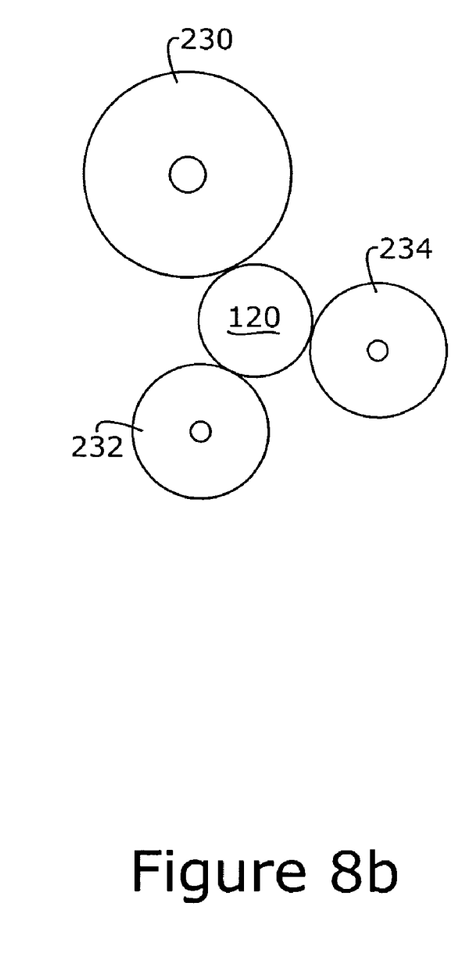
FIG. 8b is a top schematic view of the label applying rolls of the label applicator.
Figure 8C:
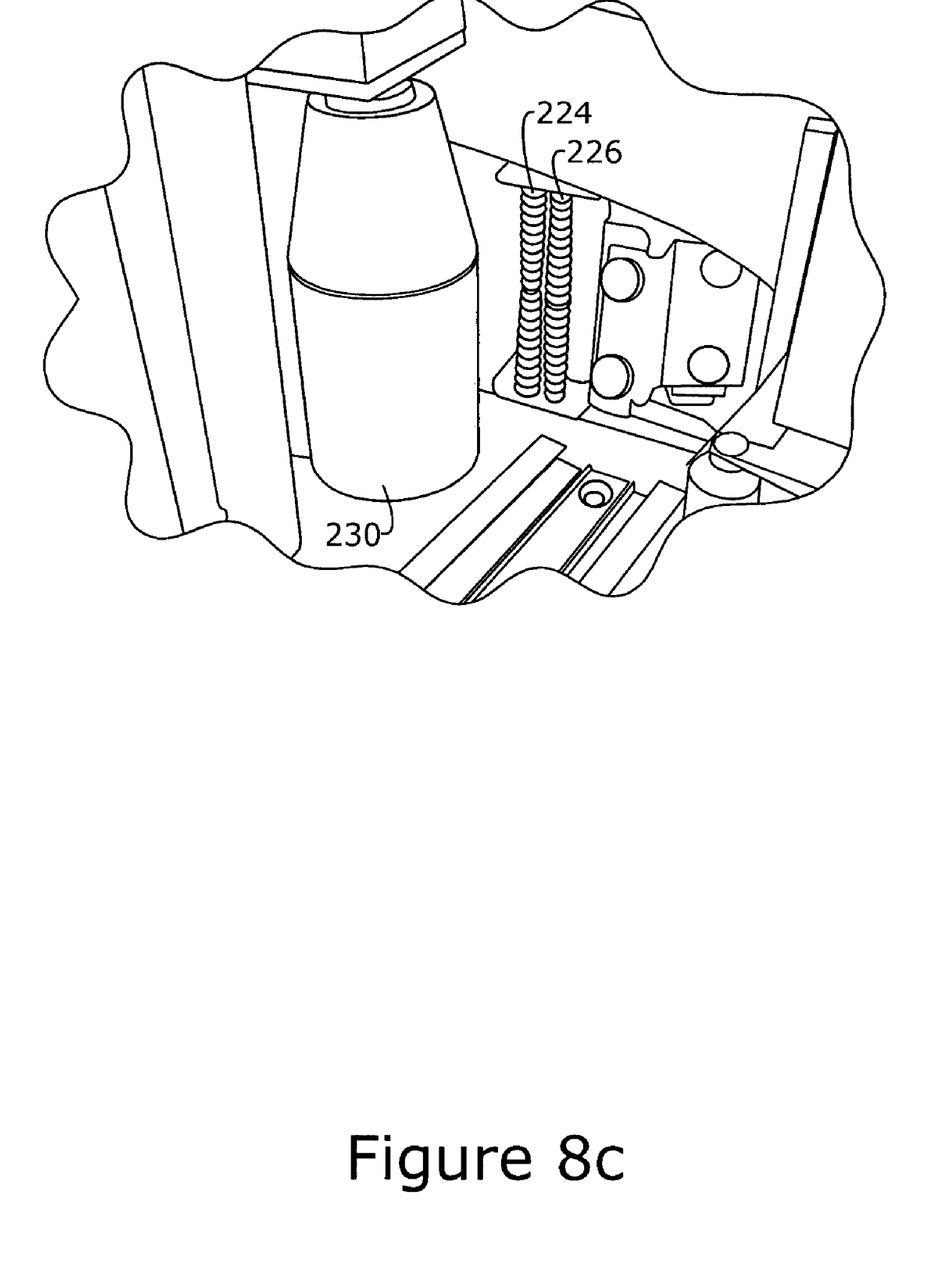
FIG. 8c is a pictorial view of a portion of the label application portion of the system of FIG. 1.

As may be seen in FIG. 8b, label 228 is then applied to vial 120 by inserting the leading edge of the label 228 into the nip between the vial and driven roller 230. The action of three rollers 230, 232, 234, surrounding vial 120 traps vial 120 in a stable, triangular fashion. Roller 230 is typically formed from a soft elastomer, for example: 40 Shore A cast urethane.

A conveyor 186 is adapted to transport labeled vials 190 to a first staging platform 188.

A second gantry 194 is adapted for rotation about its own vertical axis by a stepper motor 240 under control of PLC 148. Such gantries are known a Y-theta gantries or robots. A vertical toothed belt 198 within second gantry 194 is operatively connected to mechanism 200 and adapted to move mechanism 200 up and down. Toothed belt 198 is driven by toothed wheel 241 which is connected to stepper motor 242 under control of PLC 148. Toothed belt 198 is tensioned against toothed idler 196 at the bottom of second gantry 194. Mechanism 200 includes a stepper motor 202 having a pinion gear adapted for interaction with a rack, not shown, on a horizontal member 204. Horizontal member 204 may be moved axially away and toward second gantry 194. Second grippers 206 are disposed at a distal end of horizontal member 204. Second grippers 206 are adapted for interaction with a filled, labeled vial 208 on a second staging platform 192.

One or more vial capping mechanisms 210 are optionally disposed beneath PLC 148. In some applications, vial capping is not required; consequently, in those configurations vial capping mechanisms 210 are not included.

Third and fourth staging platforms 212a, 212b are adapted to receive either filled, labeled vials 208 or, optionally, filled, labeled and capped vials 214 from second grippers 206. The choice of third staging platform 212a or fourth staging platform 212b is determined by computer 174 and depends upon the desired destination of the filled, labeled, and optionally capped vial 214.

Swinging doors 216a, 216b are disposed proximate third and fourth staging platforms 212a, 212b, respectively. Swinging doors 216a, 216b are typically pneumatically actuated and adapted to transport labeled, filled and optionally capped vials 214 from respective third and fourth staging platforms 212a, 212b onto conveyor belts 218a, 218b, respectively.

Figure 9:
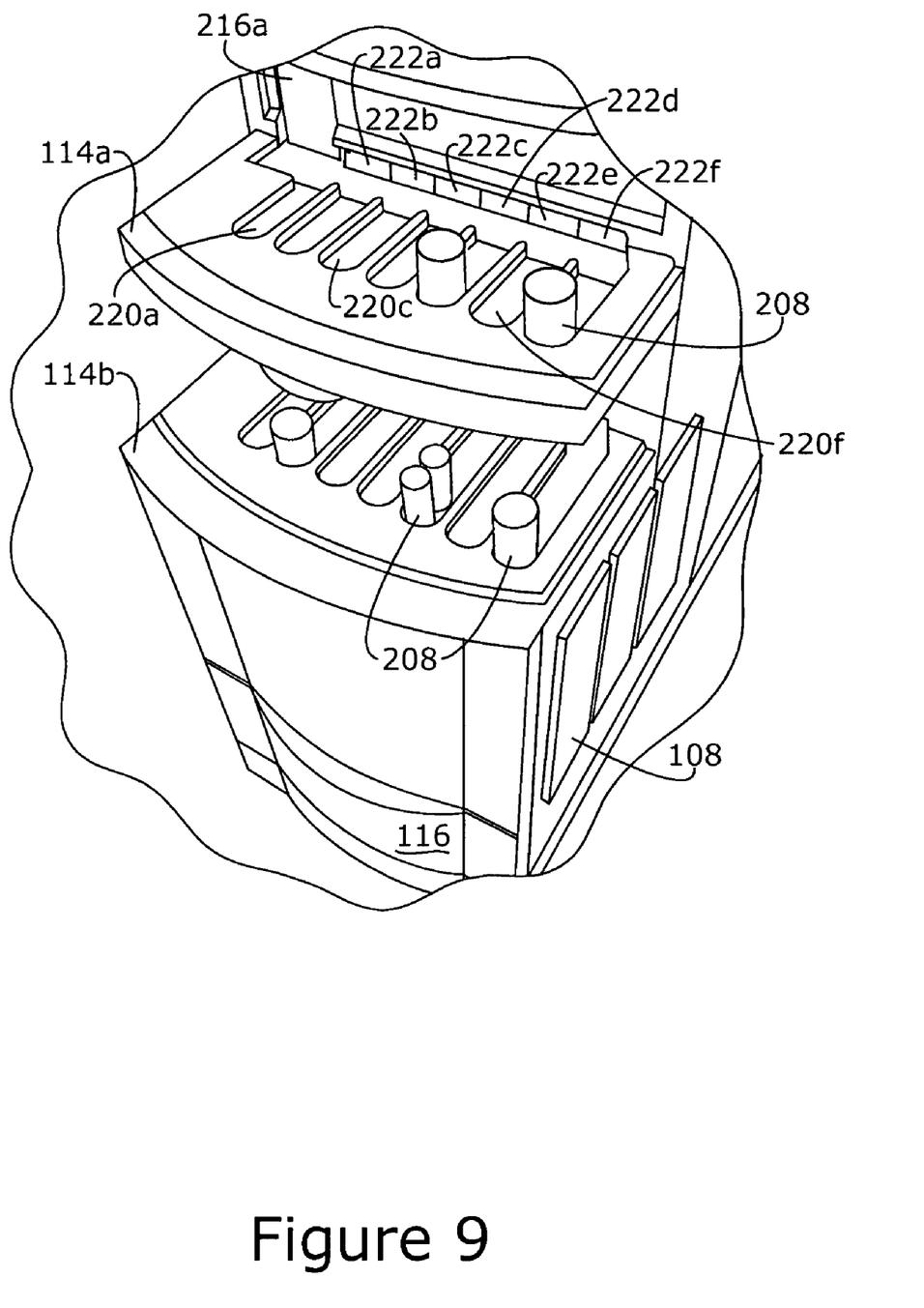
FIG. 9 is a perspective, pictorial view of a portion of the end of the system of FIG. 1 showing the sorting conveyors and vial accumulation lanes.

A plurality of sorting conveyors 220a, 220b, 220c, 220d, 220e, 220f, 220g, are disposed perpendicularly to conveyor belt 218a. A second group of sorting conveyors 220h, 220i, 220j, 220k, 220l, 220m, 220n, are disposed perpendicularly to conveyor belt 218b. A plurality of diverters 222a-222l are disposed adjacent conveyor belts 218a, 218b and adjacent respective ones of sorting conveyors 220a-220g, and 220h-220n. Diverters 222a-222l are typically pneumatically actuated under control of PLC 148.

In operation, upon a command from computer 174, one of the plurality of automated dispensers 104 is instructed to count out a specified number of the pills, tablets, or capsules, not shown, contained therein to fill a single prescription. Any or all dispensers 104 can simultaneously and independently count. When the particular dispenser 104 has finished counting for the particular prescription, and the tablets have been accumulated in the output chute, not shown, of the automated dispenser 104, an empty vial 120 of the correct size is requested by computer 174 through PLC 148. Under the control of PLC 148, the cassette 108 containing vials 120 of the calculated correct size for the prescription currently being filled releases a vial 120 onto conveyor belt 176. Conveyor belt 176 moves the released vial 120 to vial orienting apparatus 180 where vial 120 is rotationally manipulated upright with its open top facing upward.

The properly oriented vial 120 is dropped to label applicator 182 where a label 228 (FIG. 8a) bearing the correct information for the prescription being filled has been provided by label printer 184. A bar code reader confirms a readable and correct label has been applied.

Labeled vial 190 is next moved to first staging platform 188 by conveyor 186. Labeled vial 190 is then grasped by grippers 160 of main gantry 126 and transported to the correct automated dispenser 104 filling the prescription. Automated dispenser 104 will have finished counting tablets prior to the arrival of vial 190. Grippers 160 then move the labeled vial 190 inward toward dispenser 104, a predetermined distance under control of PLC 148 which then causes the counted tablets within the output chute, not shown, to be dumped into waiting vial 190.

Still held by grippers 160, filled, labeled vial 208 is transported to second staging platform 192 where vial 208 is deposited. Grippers 160 on main gantry 126 are now free to handle the next prescription.

Second gantry 194 is rotated about its own vertical axis to aim second grippers 206 toward vial 208 on second staging platform 192. Vertical belt 198 raises mechanism 200 to the proper height for second grippers 206 to engage vial 208 on second staging platform 192. Horizontal member 204 is then moved outward until second grippers 206 are positioned at vial 208. Second gripper 206 then grasps vial 208.

Once grasped by second grippers 206, filled labeled vial 208 is lifted, retracted, and rotated to vial capper 210 when needed. Capped, filled, labeled vial 214 is then moved by second grippers 206 to third or fourth staging platforms 212a, 212b, respectively, depending upon where the vial is to be presented to the operator, not shown, and deposited on the desired third or fourth staging platform 212a, 212b.

If capping is not required, vial 208 is moved by second grippers 206 directly to one of third or fourth staging platforms 212a, 212b, respectively, depending upon where the vial is to be presented to the operator and deposited on the desired third or fourth staging platform 212a, 212b.

Automated dispensing system 100 sorts filled vials 208 based upon a criteria (e.g., name, address, phone number, Social Security Number, etc.) selected by the user so that multiple prescriptions for a single customer may be properly grouped as desired.

Swinging door 216a, 216b moves vial 208 or 214 (depending upon whether the vial was capped) onto conveyor belt 218a, 218b. Conveyor belt 218a, 218b moves horizontally at right angles to the plane of automated dispensers 104. One of diverters 222a-222l then directs vial 208 or 214 onto a predetermined one of sorting conveyor belts 220a-220n, respectively. Monitor 112 displays a graphic representation of both upper and lower sorting conveyor belts, identifying the exact position of every prescription. The operator may search for the status of any prescription, and if completed the graphic will highlight or otherwise identify the exact placement of the vial or vials 208 or 214 so requested. The vials 208 or 214 may then be checked using display 112 and keyboard 118 as required. Vials 208 or 214 may be removed from sorting conveyor belts 220a-220n for further manual processing, packaging, etc. The checking operation can include the use of a built-in bar code scanner, not shown, which further helps confirm that the correct vial has been selected for checking.

As previously discussed, the automated dispensing system 100 pipelines the prescription filling operation so that a vial 120, 190, 208, or 214 is typically in process at each of the stations or steps simultaneously.

PLC 148, which coordinates and directs the above actions, is interfaced to computer 174. PLC 148 receives initiating and location commands (vial size, dispenser, and output lane), and sends status commands back to the computer 174. Computer display 112 is provided so that computer 174 may inform the pharmacy technician, not shown, of relevant facts, for example: the status of dispensers 104 and vials 120, 190, 208, 214; and the status of all orders: pending, in process, and complete.

An additional benefit of the inventive architecture (both mechanical and software) is that computer 174 can control the dispensers 104 independently of PLC 148. This means that robotic filling can be suspended and manual filling can continue. Should there be a problem with the automated system (running out of the rolls of label stock for example), the entire system need not be shut down. With the robotic filling suspended, bi-fold doors 124 can be opened, exposing the fronts of dispensers 104. Computer 174 can command the dispensers to count out prescriptions, and the operator can manually place a labeled vial at the output chute of the appropriate dispenser 104 (identified by a flashing light, not shown, on the front of the dispenser 104) and retrieve the medicant. All of these operations are under strict control of computer 174 utilizing barcode or similar technology to uniquely control the steps of retrieving a prescription so as to improve accuracy and reduce errors. This manual mode also maintains accurate inventory in dispensers 104, allows normal replenishing of dispensers 104, and allow the pharmacy to service its customers.

Since other modifications and changes varied to fit particular operating requirements and environments will be apparent to those skilled in the art, the invention is not considered limited to the examples chosen for purposes of disclosure and covers all changes and modifications which do not constitute departures from the true spirit and scope of this invention.

Having thus described the invention, what is desired is to be protected by Letters Patent as presented in the subsequently appended claims.

What is claimed is:

1. An automated prescription filling system, comprising:
   a) a vial storage cassette holding empty vials of a single size and having means for dispensing a single vial therefrom upon command;
   b) means for printing and applying a label to said dispensed, single vial, operatively connected to said vial storage cassette;
   c) a plurality of automated, independently operating dispensers, each containing a supply of a predetermined medicant and each dispenser comprising means for counting, upon command, a predetermined quantity thereof into an output chute;
   d) a robot adapted for simultaneously moving a labeled vial from said means for printing and applying a label to a particular one of said plurality of automated dispensers, for positioning said labeled vial at said discharge chute thereof, for releasing said counted medicant into said empty labeled vial, and for transporting a filled vial to an output station, all occurring in parallel, wherein said robot comprises at least one selected from the group: an X-Y gantry, and a Y-theta gantry, each having a first gripper adapted for gripping a vial operatively connected to and positionable thereby;
   e) at least one additional robot selected from the group: a robot rotatable around a central, vertical axis thereof, and an X-Y gantry, each having a second gripper adapted for gripping a vial operatively connected to and positionable thereby; and
   f) at least one staging platform accessible to at least one of said first gripper and second gripper.

2. The automated prescription filling system as recited in claim 1, further comprising:
   g) a controller operatively connected to at least one of said means for printing, said plurality of automated dispensers, and said robot.

3. The automated prescription filling system as recited in claim 1, further comprising:
   g) a computer workstation comprising at least one of the group: a pharmacy workflow interface, and an operator interface.

4. The automated prescription filling system as recited in claim 1, wherein said automated prescription filling system comprises means for identifying a size of said empty vials contained therein to said automated prescription filling system.

5. The automated prescription filling system as recited in claim 4, wherein said means for identifying a size of said empty vials contained therein comprises at least one selected from the group: a notch in an external surface of said vial storage cassette, a dimple in an external surface of said vial storage cassette, another identifiable mechanical feature in an external surface of said vial storage cassette, an RFID device, a color code, a pattern of magnets, and a bar code.

6. The automated prescription filling system as recited in claim 4, wherein said vial storage cassette is removable from said automated prescription filling system.

7. The automated prescription filling system as recited in claim 1, wherein said vial storage cassette comprises at least one independent vial storage cassette, each of said at least one cassette being removable from said automated prescription filling system.

8. The automated prescription filling system as recited in claim 1, wherein said means for applying a label comprises means for forming a dihedral in said label prior to application thereof to a vial.

9. The automated prescription filling system as recited in claim 1, wherein said means for applying a label comprises at least one resilient, elastomeric roller interacting with at least one other roller, said at least one resilient, elastomeric roller and said at least one other roller being disposed to surround and contact an outer, vertical surface of said vial, thereby applying a label intermediate said outer, vertical surface and said at least one resilient, elastomeric roller and said at least one other roller to said outer, vertical surface.

10. The automated prescription filling system as recited in claim 1, wherein said first gripper of said X-Y gantry is adapted to at least selectively position a vial at said output chute of any of said plurality of automated dispensers.

11. The automated prescription filling system as recited in claim 1, further comprising means for orienting a vial to a predetermined orientation disposed between said vial storage cassette and said means for applying a label.

12. The automated prescription filling system as recited in claim 1, wherein said plurality of automated dispensers is disposed within a frame, substantially one half of said plurality of dispensers being disposed in a first region of said frame and approximately one half of said plurality of automated dispensers being disposed in a second region of said frame.

13. The automated prescription filling system as recited in claim 12, wherein said plurality of automated dispenses is disposed within said frame on horizontal shelves disposed in a vertical array.

14. The automated prescription filling system as recited in claim 13, wherein said horizontal shelves may be withdrawn from said automated prescription filling system to replenish contents of at least one of said automated dispensers disposed thereupon.

15. The automated prescription filling system as recited in claim 14, further comprising means for inhibiting robot access to any automated dispenser disposed on a withdrawn shelf.

16. The automated prescription filling system as recited in claim 1, wherein said output chute of at least one of said plurality of automated dispensers is tilted relative to at least one other of said plurality of automated dispensers and said first gripper comprises means for presenting a vial to said tilted output chute.

17. The automated prescription filling system as recited in claim 1, further comprising:
   g) means for applying a cap to said filled vial.

18. The automated prescription filling system as recited in claim 3, wherein said computer workstation comprises a touch screen.

19. The automated prescription filling system as recited in claim 1, further comprising:
   g) at least two sorting conveyors adapted to receive filled, labeled vials from said robot.

20. The automated prescription filling system as recited in claim 5, further comprising:
   g) means for sorting filled vials according to a predetermined criteria and directing said filled, labeled vials to a predetermined one of said plurality of sorting conveyors.

21. The automated prescription filling system as recited in claim 20, wherein said predetermined sorting criteria comprises at least one sorting criterion selected by an operator.

22. A method of automatically filling a prescription, the steps comprising:
   a) providing an automated prescription filling system comprising: a vial storage cassette holding empty vials of a single size and having means for dispensing and orienting a single vial therefrom upon command; means for printing and applying a label to said dispensed, single vial, operatively connected to said vial storage cassette; a plurality of automated, independently operating dispensers, each containing a supply of a predetermined medicant and each dispenser comprising means for counting, upon command, a predetermined quantity thereof into an output chute; and a robot adapted for simultaneously moving a labeled vial from said means for printing and applying a label to a particular one of said plurality of automated dispensers, for positioning said labeled vial at said discharge chute thereof, for releasing said counted medicant into said empty labeled vial, and for transporting a filled vial to an output station, all occurring in parallel, wherein said robot comprises at least one selected from the group: an X-Y gantry, and a Y-theta gantry, each having a first gripper adapted for gripping a vial operatively connected to and positionable thereby; at least one additional robot selected from the group: a robot rotatable around a central, vertical axis thereof, and an X-Y gantry, each having a second gripper adapted for gripping a vial operatively connected to and positionable thereby; at least one staging platform accessible to at least one of said first gripper and second gripper; and a built-in computer workstation comprising a pharmacy workflow and operator interface;
   b) using said computer workstation, entering a prescription to be filled into said automated prescription filling system;
   c) selecting one of said plurality of automated dispensers containing a medicant in said prescription entered in said using step (b);
   d) simultaneously commanding said automated dispenser of said selecting step (c) to count a specified quantity of a specified medicant in parallel with at least one other dispenser;
   e) simultaneously releasing an empty vial from said vial storage cassette, orienting said empty vial and placing a label thereupon, said label comprising indicia related to said entered prescription of said using step (b) in parallel with another automated procedure within said automated prescription filling system;
   f) simultaneously using said robot to move said labeled vial to an output chute of said automated dispenser of said selecting step (c) with another automated procedure within said automated prescription filling in parallel system;
   g) simultaneously releasing said specified, counted medicant from said automated dispenser of said selecting step (c) into said empty, labeled vial in parallel with another automated procedure within said automated prescription filling system; and
   h) simultaneously moving said vial containing said released contents to an output region of said output station of said automated dispenser in parallel with another automated procedure within said automated prescription filling system.

23. The method of automatically filling a prescription as recited in claim 22, wherein said providing step (a) further comprises providing a vial capper, the steps further comprising:
   i) after said releasing step (g) and prior to said moving step (h), capping said filled vial.

24. The method of automatically filling a prescription as recited in claim 22, wherein said providing step (a) further comprises providing an output station comprising means for sorting filled vials, the steps further comprising:
   i) after said moving step (h), sorting said filled vial in accordance with a predetermined sorting criterion.

25. The method of automatically filling a prescription as recited in claim 22, wherein said releasing step (e) comprises releasing only a single empty vial from said vial storage cassette.

26. The method of automatically filling a prescription as recited in claim 22, wherein at least two of said selecting step (c), said commanding step (d), said releasing step (e), said using step (f), said releasing step (g), and said moving step (h), are performed in parallel with one another.

\* \* \* \* \*